United States Patent [19]
Benitez

[11] Patent Number: 5,505,949
[45] Date of Patent: Apr. 9, 1996

[54] TOPICAL TREATMENT FOR ACNE

[76] Inventor: Juan E. Benitez, 911 S. Airport Dr., Weslaco, Tex. 78596

[21] Appl. No.: 322,691

[22] Filed: Oct. 13, 1994

[51] Int. Cl.$^6$ .................................................. A61K 7/48
[52] U.S. Cl. .......................................... 424/401; 514/859
[58] Field of Search ............................. 424/401; 514/859

[56] References Cited

U.S. PATENT DOCUMENTS 4,557,934  12/1985  Cooper ..................................... 424/128

*Primary Examiner*—Jyothsna Venkat
*Attorney, Agent, or Firm*—Michael I. Kroll

[57] ABSTRACT

The present invention relates to a topical acne cream having primary ingredients such as: clortrimazole being an antifungal ingredient usually termed fungicidal due to its characteristic of killing fungus when they come in contact with the substance; betamethasone dipropionate being an anti-inflammatory ingredient; and salicylic acid being an antiseptic/anti-bacterial/keratolytic substance which rapidly reduces inflammation caused by a person's body's immune reaction to acne bacteria as well as optional secondary ingredients such as binders, emulsifiers and fillers which may be present individually and in combination.

1 Claim, 2 Drawing Sheets

TOPICAL TREATMENT FOR ACNE

BACKGROUND OF THE INVENTION

Field of the Invention

The present invention relates to the field of treating the skin condition known as acne. More specifically, the present invention is concerned with the prophylactic or therapeutic topical treatment of acne. Even more specifically, the present invention is concerned with the topical treatment of such skin disorders as acne vulgaris, other acneiform dermal disorders, e.g. preadolescent acne, acne rosacea (now known as rosacea), premenstrual acne, acne venenata, acne cosmetica, pomade acne, acne detergicans, acne cosmetica, acne excoriee, gram negative acne, steroid acne, acne conglobata, or nodulocystic acne. The present invention can also be used for topically treating certain other types of acneiform dermal disorders, e.g. perioral dermatitis, seborrheic dermatitis in the presence of acne, gram negative folliculitis, sebaceous gland dysfunction, hiddradenitis suppurativa, pseudo-folliculitis barbae, or folliculitis.

The present invention relates to topically applied medicinal compositions, and more particularly refers to such compositions having active topical medicinal ingredients, and additionally having LYCD in amounts sufficient to act with the other active ingredients to provide synergistic therapeutic results.

The present invention concerns benzoyl peroxide quaternary ammonium lipophilic salicylate based pharmaceutical and cosmetic compositions and their use especially in treatment of acne.

DESCRIPTION OF THE PRIOR ART

Acne vulgaris is a common disease which afflicts approximately 90% of all teenagers, and, not uncommonly, affects men and women in their twenties or thirties or may persist in adults for many years. Acne vulgaris most commonly occurs on oily areas of the skin with high sebaceous gland concentration. The areas of high sebaceous gland concentration are the face, ears, retroauricular areas (e.g. behind the ears), chest, back, and occasionally the neck and upper arms.

Acneiform eruptions can occur wherever there is a pilosebaceous unit or sebaceous follicle which does include the entire surface of the skin. The basic lesion in acne is the comedo commonly known as the blackhead. The comedo is created by retention of layers of dead skin known as keratin in the lining of the follicles. In addition to hyperkeratosis (which is thickening or retentative layering of keratin), there is an accumulation of sebum which is the lipid-laden product of the sebaceous gland. The cells of the sebaceous glands in which sebum originates are the sebocytes. The combination of the keratin and the sebum produces a plugging of the mouth or opening of the follicular canal, and papules are formed by inflammation around the comedones (plural of comedo). Depending upon the degree of inflammation, pustules, cysts, nodules, granulomatous reactions, scars, and keloids may develop.

Most typical forms of mild acne vulgaris demonstrate the predominance of comedones with the occasional pustules. Pustules and papules predominate in more severe cases. These can heal with scar formation; that is, fibrosis of the lesions which are deep and penetrating. In moderately active cases, larger cystic lesions can develop.

Acne vulgaris can appear in many clinical varieties. The mildest case manifests comedones on oily skin and is called acne comedo.

Papular acne is another variety of acne which has many inflammatory papules.

This form of ache is common in adolescent skin, but it can be seen in all ages. The papular inflammatory form of acne can progress to an indurated, deeper, and destructive form known as acne indurata. These lesions can produce severe scarring and can be quite deep seated and destructive.

Steroid acne vulgaris can occur when oral corticosteroids or topical steroids are used and occurs as inflammatory follicular papules. When oral corticosteroids are ingested, the inflammatory papules are usually sudden in appearance and can cover the chest, back, arm, and face. When topical corticosteroids are used for more than two weeks, a localized inflammatory apular response can develop which can proceed to a granulomatous chronic reaction known as steroid acne rosacea.

Premenstrual acne can occur in a large number of menstruating women as a papular and pustular acne vulgaris, approximately one week prior to menstruation. There is a body of evidence that implicates a surge in progesterone as the mediator of premenstrual acne.

Preadolescent acne is divided into neonatal, infantile, and childhood forms of acne. The neonatal form is limited to the first few weeks of life. It usually develops a couple of days after birth. It more commonly afflicts males and reveals transient facial papules and pustules which can clear spontaneously in a few days or weeks. The stimulation of neonatal sebaceous glands by circulating maternal progesterone appears to be the cause.

If the acne persists beyond the first month of life, the acne is called infantile acne and can extend into childhood, adolescence, and adult life. The childhood acne can result from a persistent infantile acne or can develop de novo after age two. This form of acne is uncommon, but it has more of a male predilection. It is characterized by comedones commonly in groups, papules, pustules, and, rarely, cysts. This condition can extend from a few weeks to several years and can develop into pubertal acne.

Acne venenata is by definition a comedonal or papular acne which occurs after exposure to chlorinated hydrocarbons (chloracne), cutting oils, petroleum oil, coal tar, and pitches.

Acne cosmetica is a persistent low grade comedonal and/or papular and pustular acne that occurs usually on the chin and cheeks of adult women due to oil-based cosmetics, i.e. foundations, facial creams, and sunscreens.

Pomade acne is a type of acne cosmetica which appears to occur almost exclusively in black persons who apply grease and oil to scalp hair and the face as a grooming aid. The lesions are predominately comedonal acne and can develop into inflammatory acne papules, depending upon the chronicity of the pomade use.

Acne detergicans occurs as a type of comedonal acne in patients who use oil-based cleansing soaps. Acne excoriee, also known as pickers acne, starts out as a mild form of papular or comedonal acne which is manipulated or picked and causes further inflammation, more papules, and sometimes scars, pitting, and atrophy of the skin.

Gram negative acne, sometimes called gram negative folliculitis when it extends to the neck, arms, legs, and trunk, is a form of an inflammatory papular, follicular, and pustular response to gram negative organisms including Enterobacter, Klebsiella, Escherichia, Proteus, Serratia, and Pseudomonas. The most characteristic lesion on the face are superficial pustules, or papulo-pustules (which is a combination of a papule and pustule). The face can show diffuse erythema and inflammation surrounding these pustules and juicy papules or papulo-pustules.

The gram negative acne is usually highly resistant and usually occurs in patients who have bad inflammatory papular acne for long periods or who have been treated with long term oral administration of antibiotics such as tetracycline, erythromycin, or minocycline or topical antibiotics such as topical clindamycin or topical erythromycin. Subsequent to the oral administration of tetracycline or erythromycin, oral administration of amoxicillin, ampicillin, and trimethoprim-sulfomethoxazole has been shown to be effective in treating this disease. (Poli, F., Prost, C., Revuz, J., Gram-negative Folliculitis, Ann. Dermatol. Venereol., 115:797–800, 1988).

In another reference, Marks, R. and Ellis, J., "Comparative effectiveness of tetracycline and ampicillin in rosacea", Lancet, 1971, vol. 2, pages 1049–1052, there is a disclosure that ampicillin has been used orally for treatment of rosacea. More specifically, orally administered ampicillin was compared with orally administered tetracycline in the treatment of rosacea.

Furthermore, in the personal experience of one of the inventors, in his capacity as a practicing dermatologist, in treating well over 200 patients, oral ampicillin taken in the form of an oral capsule between 500 mg and 1 gm each day for one month greatly improves this condition. Before treatment with ampicillin orally, the patients appear to have inflammatory papules and pustules present, and treatment of this clinical subset of acne vulgaris appears to have good success with the oral ampicillin.

However, unwanted side effects often occur with the oral administration of ampicillin (and amoxicillin). For example, unwanted side effects from oral administration often include diarrhea, cramping, and nausea. It would be desirable, therefore, to provide a treatment with ampicillin (and amoxicillin) which does not result in the unwanted side effects stated above.

Acne rosacea is an inflammatory eruption that is chronic and occurs on the face, especially on the nose as well as the scalp and neck, in some instances. It is manifested by erythema, pustules, papules, telangiectasia (which is dilation of superficial capillaries), and hypertrophy of sebaceous glands. The middle portions of the face are most frequently involved. The eyes and eyelids are not uncommonly involved and can produce inflammation and infection of the conjunctiva, eyelids, and hypertrophy of the meibomian glands. Acne rosacea is often called simply rosacea and is most common in middle aged women and men. Rosacea can go on to form a granulamatous rosacea which is characterized by resistant inflammatory papules which when biopsied reveal non-caseating epithelial cell granulomas.

Pseudofolliculitis barbae is a predominantly male affliction which is characterized by inflammatory papules and pustules on the bearded area of the face most commonly in black persons, but all racial groups can be affected. The mechanism is thought to be an inflammatory response to the end of hair (usually curly beard facial hair) into the skin causing a foreign body inflammatory response.

Folliculitis is an inflammatory reaction around the hair follicle which can be bacterial or non-bacterial in nature. Predominately, folliculitis is caused by gram positive organisms such as Staphylococcus and Streptococcus, and less frequently by gram negative bacteria discussed hereinabove with respect to gram negative folliculitis.

Perioral dermatitis is a common papular inflammatory eruption which is confined around the mouth. It most commonly afflicts women in their early twenties to middle thirties, but it can be seen in adolescents and more mature adults.

Hiddradenitis suppurativa is a suppurative (chronic) and cystic disease of apocrine gland regions of the skin, including the axillae, perineum and groin.

There is a genetic tendency to acne, in particular acne congoblata which is a deep cystic and sinus forming type of acne. This condition is essentially a deep, aggressive form of cystic acne occurring in the apocrine gland regions. Topical administration of clindamycin has been used to treat this form of cystic acne.

The etiology of acne vulgaris and related disorders as discussed above is not completely known in every detail. However, what is known is that acne, in general, is caused by a plurality of factors. In general, there are four main factors that cause acne: genetics; hormonal activity; bacteria; and the inflammatory response.

Genetics is a prominent component as it is well known that several members of the same family can be affected with moderate to severe scarring acne. The inheritance by some is thought to be autosomal dominant, but this has not been definitively proven. Furthermore, on the molecular level, there has not yet been discovered a gene or group of genes that are responsible for the various forms of acne vulgaris.

Another key factor in the development of acne is hormonal. In adolescence, for example, it is thought that androgens can interact with receptors on the sebaceous glands and cause stimulation of the sebaceous gland, to hypertrophy and hence form more sebaceous production of lipids and free fatty acids which distend the follicular canal. More specifically, there is evidence for increased peripheral metabolic conversion of the androgen testosterone to dihydrotestosterone at the level of the skin in acne patients. It is further hypothesized that receptors on the sebaceous gland for the active androgen dihydrotestosterone can exhibit various degrees of sensitivity, and that a heightened sensitivity response may be partially or entirely genetically predetermined.

Another causative factor in acne is the presence of bacteria in the follicular canal. Within the follicular canal are bacteria which are indigenous to the follicular lining. Among the bacteria flora present are anaerobic, gram positive organisms called Proprionibacterium acnes. It is interesting to note that they are present in abundance in pathologically affected sites. They are reduced during oral antimicrobial treatment, and their absence from nonhuman animal skin is striking especially since animals do not exhibit acne vulgaris.

Yet another causative factor in acne is the inflammatory response manifested in the skin. More specifically, it is thought that Proprionibacterium acnes lives in symbiosis on the keratin lined follicular canal. Proprionibacterium acnes ingests the sebum produced from the sebocytes of the sebaceous glands. This nascent sebum is largely lipid in composition and also contains DNA, RNA, proteins, and other cellular components that result from the breakdown of sebocytes themselves. The Proprionibacterium acnes which are highly lipophilic, feed on the nascent sebum. It has been shown that Proprionibacterium acnes are found only in sebaceous rich areas. If the nutrients increase due to an active and large sebaceous system, then colonization and high growth rates of Proprionibacterium acnes will form. It has been shown that the resident bacterial flora will produce biologically active molecules such as histamine, extracellular enzymes, and peptides which may be responsible for the chemotaxis of the inflammatory infiltrate in acne vulgaris. Since the follicular lining in the pilosebaceous unit is intact, it has been theorized that if colonization of Proprionibacterium acnes occurs in sufficient numbers, they could produce initiating antigenic molecules that promote the initiation of inflammation. Proprionibacterium acnes can produce proteinases, lipase, and hyaluronate lyase all of which may serve as the catalysts or initiators of the inflammatory infiltrate which has been shown to be composed of neutrophils and lymphocytes.

A number of treatments are presently known for treating acne, some more successful than others. Some modes of treatment have been mentioned above. There are two modes of treatment, topical and systemic.

Aside from treatments mentioned above, some additional systemic treatments for acne that are presently employed are: oral tetracycline; oral erythromycin; minocycline; doxycycline; oral trimethoprim-sulfamethoxazole and isotretinoin.

Those that have been suggested in the past and that re no longer generally employed include: antibacterial vaccines; estrogen therapy; dietary restrictions; and vitamin therapy (e.g. oral ingestion of vitamin A).

Some of the topical treatments that are presently employed are: topical erythromycin, clindamycin, benzoyl peroxide, 2% sulfur, 3% resorcinol, a tetracycline derivative (meclocycline sulfosalicylate 1%), 2% salicylic acid, and tretinoin.

Topical treatments that have been suggested in the past and that are no longer generally employed include: x-ray treatment; electric sparks; vitamin therapy; treatment with a plant extract as described in U.S. Pat. No. 4,803,069.

More specifically with respect to the topical use of certain specific antibiotics, a topical solution, ointment, and gel containing erythromycin is used. Also used is a topical solution, gel, and otion containing clindamycin, and a cream containing meclocycline sulfosalicylate 1% (a tetracycline derivative).

Some of the undesirable side effects of orally administered antibiotics are abdominal cramps, black tongue, cough, diarrhea, fatigue, irritation of the mouth, loss of appetite, nausea, vomiting, fever, hearing loss, jaundice, rash, rectal and vaginal itching, and superinfection.

It is noted that erythromycin is produced by the bacterium Streptomyces erytheus and that erythromycin has a chemical structure that is substantially unique to erythromycin and its derivatives. The molecular weight of erythromycin A is 733.92. The empirical formula for erythromycin A is $C_{37} H_{67} NO_{13}$ having a 60.55% carbon content, a 9.20% hydrogen content, a 1.91% nitrogen content, and a 28.34% oxygen content.

Clindamycin has a chemical structure indicated by its chemical name which is methyl 7-chloro-6,7,8-trideoxy-6-[[(1-methyl-4-propyl-2 -pyrrolidinyl)carbonyl]amino]-1-thio-L-threo-alpha-D-g alacto-octopyranoside. The molecular weight of clindamycin is 424.98. The empirical formula for clindamycin is $C_1 H_{337} ClN_2 O_5 S$ having a 50.87% carbon content, a 7.83% hydrogen content, a 8.34% chlorine content, a 6.59% nitrogen content, a 18.82% oxygen content, and a 7.54% sulfur content.

Other topical treatments for acne using antibiotics are described in the following Great Britain patents: neomycin, G. B. Pat. No. 1,054,124; erythromycin, G. B. Pat. No. 1,587,428; and erythromycin derivatives in conjunction with benzoyl peroxide, G. B. Pat. Nos. 2,088,717 and 2,090,135.

Still another topical treatment for acne, more specifically acne vulgaris, includes preparation of a hyaluronic acid derivative which is a bridged conjugate of hyaluronic acid (which is a linear polymer of N-acetyl glucosamine and glucuronic acid units) bonded to a bridging agent (which is cyanogen bromide) which, in turn, is bonded to the amino-nitrogen atom of the aminopenicillin, ampicillin. Thus, with this hyaluronic acid derivative, the amino-nitrogen of the aminopenicillin is no longer in the form of a primary amino group. This hyaluronic acid derivative is disclosed in Great Britain Published Application 2,207,142.

The formulation disclosed in Great Britain Published Application 2,207,142 may pose several significant problems. First, by reacting the bridging agent with the primary amino-nitrogen of the aminopenicillin, the effectiveness of the aminopenicillin may be severely reduced or even eliminated. More specifically, presently, all of the aminopenicillins that are approved for prescribing in the practice of medicine in the United States include an amino-nitrogen which is in the form of a primary amino group (the nitrogen atom of the primary amino group being bonded to two hydrogen atoms). Not one of these approved aminopenicillins has its characteristic primary amino group modified so that it is no longer a primary amino group.

Another significant potential problem posed by the hyaluronic acid derivative is disclosed in Great Britain Published Application 2,207,142 is the fact that a very toxic bridging agent, cyanogen bromide, is disclosed. Cyanogen bromide can cause toxic effects similar to those of hydrogen cyanide. Hydrogen cyanide may cause death from only a few minutes exposure to a concentration of approximately 300 ppm. (See Merck Index, Tenth Edition, 1983, pages 385 and 696) Lesser concentrations may cause headache, vertigo, nausea, and vomiting. With these potentially serious toxic side effects of cyanogen bromide, it may be undesirable if not risky to even employ the hyaluronic derivative disclosed in Great Britain Published Application 2,207,142. More specifically, on page 5, lines 3–5 of Great Britain Published Application 2,207,142, there is a teaching that a stringy precipitate (of a bridged hyaluronic acid/cyanogen bromide/ampicillin conjugate) is washed several times with absolute ethanol and dried in the air. Then, as disclosed on page 5, lines 16–26, the bridged hyaluronic acid/cyanogen bromide/ampicillin conjugate, having been incorporated in a conventional medium, is applied directly to the skin to treat acne vulgaris. What may be risky about using this bridged hyaluronic acid/cyanogen bromide/ampicillin conjugate is that a quantity of unreacted cyanogen bromide may remain as a residue in the precipitate after several rinses with absolute alcohol. Then, by applying some of this bridged hyaluronic acid/cyanogen bromide/ampicillin conjugate directly to the skin of patients, one may then be applying a residue of cyanogen bromide directly to the skin of patients.

For the reasons stated above with respect to the bridged hyaluronic acid/cyanogen bromide/ampicillin conjugate disclosed in Great Britain Published Application 2,207,142, it is desirable to avoid using an ampicillin in which the characteristic amino-nitrogen is not in the form of a primary amino group, and it is desirable to avoid using a material that may contain a toxic residue such as the bridging agent cyanogen bromide.

Still other topical treatments for acne using anti-bacterials are described in the following U.S. patents: an azole derivative in conjunction with benzoyl peroxide, U.S. Pat. No. 4,446,145, incorporated herein by reference; and metronidazole in a special gel as described in U.S. Pat. No. 4,837,378, incorporated herein by reference.

LYCD as utilized herein in the specification and claims is the acronym for Live Yeast Cell Derivative. The material is also known as Skin Respiratory Factor (SRF), Tissue Respiratory Factor (TRF), and Procytoxoid (PCO). The product, LYCD, is an alcoholic extract of viable Saccharomyces cerevisiae. The material is produced and marketed by MDH Laboratories, Inc., Cincinnati, Ohio 45210 as a standard article of commerce. Another producer of LYCD is Universal Foods Corporation, Fermentation Division, Milwaukee, Wis. 53202. LYCD is available for experimental use as a bulk drug assaying 5 units to 40 units/mg of respiratory activity. In topical medicinal preparations it is characterized and quantified in terms of Skin Respiratory Factor (SRF) units. A unit of activity is calculated as the amount of SRF which is required to increase the oxygen uptake of 1 mg of dry weight rat abdominal skin by 1 percent at the end of a 1 hour testing period in a Warburg apparatus.

LYCD is also available as LYCODERM.RTM. ointment containing 2,000 units Skin Respiratory Factor (SRF) per ounce, from Arel Pharmaceuticals, Inc., Cincinnati, Ohio. In the prior art the well know hemorrhoidal ointment, PREPARATION H.RTM., contains 2000 units of SRF (ca 1%) per ounce of ointment. J. Z. Kaplan (Arch. Surge. 119(9) p. 1005–8 (1984) has reported that, in a double blind human skin graft study donor sites treated with LYCD ointment, statistically significant earlier angiogenesis and epitheliazation occurred as compared with donor sites in the same patients treated with ointment bases (without LYCD). This study confirmed earlier laboratory reports such as that of Wm. Goodson et. al. Journal of Surgical Research 21: 125–129 (1976) showing that LYCD is capable of stimulating wound oxygen consumption, epitheliazation, and collagen synthesis.

As reported in the Cincinnati Inquirer of Dec. 12, 1986, Ashlley Hunter Cosmetic Co. offers a facial cream containing LYCD to minimize wrinkles. For milder forms of acne, which may be inflammatory, topical benzoyl peroxide (BP), an antibacterial and oxidizing agent, topical erythromycin (EM), clindamycin phosphate (CP), oral tetracyclines, or EM antibiotics are usually effective treatments, as disclosed in the prior art. (C. D. Bunker, Drugs Today, 24, 229 (1988).

The etiopathology of acne, although unclear, starts in formation of a characteristic lesion: the comedo. This produces a blockage in the pilosebaceous canal following dyskeratinization of the infundibular zone of the canal. A major effect of the blockage is to modify the rheology of the sebum and the physicochemical properties of the area. Such modification allows resident cutaneous strains to hyperproliferate which in turn triggers an inflammation reaction in the organism.

Benzoyl peroxide has been known for several years to be a particularly interesting keratolytic agent among recognized therapeutic acne treatments. In addition, it has good bacteriostatic properties.

Use of standard antibiotics in acne treatment is also widespread. They do, in fact, shown considerable bacteriostatic and anti-inflammatory activity. Orally administered active antibiotics are numerous. Among these, clindamycin and especially erythromycin show topical activity.

Antibiotics have previously been combined with benzoyl peroxide in order to increase the activity of topical anti-acne compositions. In particular, erythromycin has already been combined with benzoyl peroxide (French patent F 77 021 57).

However, a major drawback of the use of antibiotics (either alone or in combination with benzoyl peroxide) lies in their prolonged use whereupon bacterial flora become resistant, rendering the antibiotics less effective in subsequent treatment l(LEADEN, J. J; J. Am. Aced. Dermatol. 8 (1) 41–45

Further, benzoyl peroxide-erythromycin combinations are unstable over periods of time.

Quaternary ammonium compounds (M. GLOOM, Arch. Dermatol. Res. 265 207–212 (1979)) have been envisaged as replacements for antibiotics in topical treatment of acne. It has been shown that certain quaternary ammonium compounds are as effective as antibiotics against the main strains responsible for acne, without inducing resistance.

Combining benzoyl peroxide with quaternary ammonium compounds for topical treatment is also known (French patent F 73 29 233). In such compositions, benzoyl peroxide acts by decomposing to liberate active oxygen in situ. Compositions, which comprise benzoylperoxide as an active ingredient, are considered to be amongst the most effective ones in the treatment of acne vulgaris (see, for example, J. J. Leaden and A. M. Kligman, Drugs, 12, 292–300 (1976)). To improve the effect of benzoylperoxide there are frequently added to the compositions other known anti-acne substances. For example, as described by S. Hurwitz in Cutis 17, 85–590 (1976), there is a substantial increase in the therapeutic effect when benzoylperoxide is used in combination with retinoic acid. Considerable disadvantages of such compositions are, however, that they frequently cause allergic contact dermatitis and/or that they are, in certain cases, extremely irritating and drying, necessitating alteration of either the frequency or the duration of the applications or the concentration of the active ingredients in the composition.

Especially in the treatment of patients with inflammatory lesions, benzoylperoxide is often used in combination with orally administered antibiotics, e.g., tetracycline, erythromycin and the like. However, many questions have been raised concerning the safety of short- and long term use of orally administered antibiotics in the treatment of acne. Moreover, as a general rule, it is desirable to avoid oral therapy in the treatment of skin diseases whenever an effective topical treatment modality is available. Compositions, which are suitable for topical administration and which comprise benzoylperoxide in combination with, for example, erythromycin, are described in French Pat. No. 2,378,523. These compositions are known to reduce the numbers of Propionibacterium acnes, the main organism involved in the acne bearing areas.

W. J. Cunliffe and D. Gould, in British Journal of Clinical Practice, Suppl. to 32 (8), 15 (1978), described an experiment wherein a cream, containing 2% of micronazole nitrate, was tested in the treatment of acne. Although a positive effect was noted it was found that the numbers of Propionibacterium acnes and Staphylococcus epidermidis on the skin were not altered, despite the in vitro activity of micronazole against Propionibacterium acnes.

The present invention is concerned with pharmaceutical compositions for the topical treatment of acne vulgaris, which compositions are not irritating and have, compared with those known in the art, an improved anti-acne activity. These compositions comprise a pharmaceutically acceptable inert carrier material and as active ingredients mutually potentiating amounts of benzoylperoxide and of at least one chemical compound selected from the group consisting of an azole derivative having the formula ##STR1## and the pharmaceutically acceptable acid addition salts thereof, wherein Q is a member selected from the group consisting of CH and N; n is 0 or the integer 1; $R^1$ is a member selected from the group consisting of lower alkanoyl, hydroxylower alkyl, phenyl and phenyllower alkyl, wherein said phenyl radicals are optionally substituted with up to 3 halo atoms;

$R^2$ is a member selected from the group consisting of aryl, aryloxy, arylthio, aryllower alkyloxy and aryllower alkylthio, wherein said aryl is selected from the group consisting of phenyl, thienyl and halothienyl, said phenyl being optionally substituted with up to 3 halo atoms; and $R^3$ is a member selected from the group consisting of hydrogen, lower alkynyl, lower alkyloxycarbonyl and phenyl, said phenyl being optionally substituted with up to 3 substituents, each independently selected from the group consisting of halo and trifluoromethyl.

In the foregoing definitions the term halo is generic to fluoro, chloro, bromo and iodo; the term "lower alkyl" is meant to include straight and branch chained hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; and the term "lower alkynyl" refers to straight alkynyl radicals having from 2 to 6 carbon atoms such as, for example, ethynyl, 2-propynyl, 2-butynyl, 3-pentynyl, 2-hexynyl and the like.

Specific examples of azole derivatives within the scope of formule (I) are the followings: 1-[2-(2,4-dichlorophenyl)-2-[(2,6-dichlorophenyl)meth
oxy]ethyl]-1H-imidazole, generically designated as isoconazole;
1-[2-(2,4-dichlorophenyl)-2-[(2,4-dichlorophenyl)meth oxy]ethyl]-1H-imidazole, generically designated as miconazole;
1-[2-(2,4-dichlorophenyl)-2-[(4-chlorophenyl)methoxy] ethyl]-1H-imidazole, generically designated as econazole;
1-[(2-chlorophenyl)diphenylmethyl]-1H-imidazole, generically designated as clotrimazole;
1-[2-(2,4-dichlorophenyl)-2-[(4-chlorophenyl)methylthio] ethyl]-1H-imidazole, generically designated as sulconazole;
1-(4-chlorophenoxy)-1-(1H-imidazol-1-yl)-3,3-dimethyl butan-2-one, generically designated as climbazole;
1-[2-(2,4-dichlorophenyl)-2-(2-thienylmethoxy)ethyl]-1H-imidazole;
1-[2-(4-chlorophenyl)-2-[(2,6-dichlorophenyl)methoxy] ethyl]-1H-imidazole, generically designated as orconazole;
1-[4-(4-chlorophenyl)-2-[(2,6-dichlorophenyl)thio]but yl]-1H-imidazole, generically designated as butoconazole;
1-(4-chlorophenoxy)-3,3-dimethyl-1-(1H-1,2,4-triazol-1-yl)-2-butanol, generically designated as triadimenol;
2-(4-chlorophenoxy)-4,4-dimethyl-1-(1H-1,2,4-triazol-1-yl)-3-pentanone;
1-[2-[(2-chloro-3-thienyl)methoxy]-2-(2,4-dichlorophenyl )ethyl]-1H-imidazole, generically designated as tioconazole;
2-(2,4-dichlorophenoxy)-1-(1H-imidazol-1-yl)-4,4-dimethylpentane-3-one, generically designated as valconazole;
1-(1,1-diphenyl-2-propynyl)-1H-imidazole; methyl .alpha.,.alpha.-diphenyl-1H- imidazole-1-acetate; and
1-[diphenyl[3-(trifluoromethyl)phenyl]methyl]-1H-1,2, 4-triazole, generically designated as fluotrimazole.

Preferred compositions according to the present invention are those wherein the azole derivative is a compound of formula (I) wherein Q is CH.

Particularly preferred compositions are those wherein the azole derivative is selected from the group consisting of clotrimazole and a compound of formula (I) wherein Q is CH, n is 1, $R^1$ is mono- or dihalophenyl, $R^2$ is (mono- or dihalophenyl)methoxy and $R^3$ is hydrogen.

Especially preferred compositions are those wherein the azole derivative is selected from the group consisting of isoconazole, miconazole, econazole, clotrimazole and the pharmaceutically acceptable acid addition salts thereof.

More especially preferred compositions are those wherein the azole derivative is selected from the group consisting of miconazole and econazole and the pharmaceutically acceptable acid addition salts thereof.

The most preferred compositions according to the present invention are those wherein the azole derivative is selected from the group consisting of miconazole and the pharmaceutically acceptable acid addition salts thereof.

The azole derivatives used as active ingredients in the aforementioned compositions are known per se. Such compounds and their preparations have been described, for example, in U.S. Pat. Nos. 4,055,652; 4,062,966; 4,078,071; 3,974,174; 3,940,413; 3,657,445; 3,870,726; 3,826,836; 3,682,950; 3,723,622; 3,812,142; 3,903,287; 3,952,002; 3,717,655 and in Belgian Pat. No. 849,012.

The compounds of formula (I) may be converted to their therapeutically active non-toxic acid addition salt form by treatment with an appropriate acid, such as, for example, an inorganic acid, such as hydrohalic acid, e.g., hydrochloric, hydrobromic and the like, and sulfuric acid, nitric acid, phosphoric acid and the like; or an organic acid, such as, for example, acetic, propanoic, 2-hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, .alpha.- hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The efficacy and the mutually potentiating effect of the compositions comprised within the scope of the present invention are clearly may be demonstrated by their in vitro activities on an examplitory bacterium such as Staphylococcus epidermidis, and Propionibacterium acnes, which microorganisms may all be recovered from the skin-lesions caused by acne vulgaris.

In vitro experiments

A. Materials and methods

1. Media

Tryptose broth contains 20 g of tryptose (Difco), 5 g of sodium chloride and 1 g of glucose per liter distilled water. Tryptose agar contains in addition 15 g agar.

2. Strains and inocula

Staphylococcus species are maintained on agar slants and subcultured twice on tryptose broth for 24 hours at 37 degree. C. A loopful is inoculated in 4.5 ml of the same medium and grown at 37 degree. C. for 64 hours. A 0.2 ml aliquot of the culture is used to inoculate 100 ml tryptose broth and cells are grown aerobically for 24 hours at 37 degree. C. by shaking in a reciprocating shaker. A 0.20 ml sample, containing 1.10.sup.9 cells are used to inoculate 100 ml of tryptose broth whereto solvent and the investigated azole derivative and/or benzoylperoxide are added.

Propionibacterium acnes B 22,267, maintained on fluid thioglycollate medium, are subcultured for 72 h. at 37 degree. C.; 0.2 ml aliquots of 48 h.-cultures (containing 5.0.times.10.sup.7 cells/ml) are used to inoculate 15 ml of the experimental fluid thioglycollate medium.

3. Growth studies

Staphylococcus species cells are grown at 37 degree. C. aerobically by shaking in a reciprocating shaker. The investigated azole derivative and/or benzoylperoxide are dissolved in dimethylsulfoxide and added to the media immediately before inoculation. Only freshly prepared benzoylperoxide solutions are used. Controls are similarly set up with equivalent quantities of dimethylsulfoxide (final concentration: 0.15%). Propionibacterium acnes B 22,267: drugs and/or solvent are also added just before inoculation. To remove oxygen from the medium, the inoculated fluid thioglycollate medium is flushed for 30 min. with oxygen-free sterile nitrogen.

4. Total count method

Samples of 0.1 ml are withdrawn from the cultures and diluted in Isoton.RTM. (Coulter Electronics) containing 1% of formaldehyde. Cells are counted by means of a Coulter counter.RTM., model ZBI-biological (Coulter Electronics).

5. Viable count method

Samples are withdrawn from the cultures at different time intervals and decimally diluted in sterile 0.85% saline. Aliquots of 0.1 ml from the undiluted and diluted suspensions are plated on each of 4 replicate tryptose-agar plates. They are then incubated aerobically for 72 h. at 37 degree. C. and the colonies are counted.

Numerous innovations for a topical acne cream have been provided in the prior art that are described as follows. Even though these innovations may be suitable for the specific individual purposes to which they address, they differ from the present invention as hereinafter contrasted.

U.S. Pat. No. 5,260,292

Topical treatment of acne with aminopenicillins

Howard N. Robinson, and Neil F. Martin

A method and composition for topically treating acne and acneiform dermal disorders includes applying an amount of an antibiotic selected from the group consisting of ampicillin, amoxicillin, other aminopenicillins, and cephalosporin, and derivatives and analogs thereof, effective to treat the acne and acneiform dermal disorders. The antibiotic is blended with a carrier suitable for topical application to dermal tissues. The carrier is selected from the group consisting of an aqueous liquid, an alcohol base, a water soluble gel, a lotion, an ointment base, petrolatum, a non-aqueous liquid base, a mineral oil base, a blend of mineral oil and petrolatum, a suspension of solid particles in a liquid, and a suspension of an ion-exchange resin in water.

U.S. Pat. No. 5,019,567

Benzoyl peroxide-quaternary ammonium lipophilic salicylate based pharmaceutical and cosmetic compositions and their use especially in treatment of acne Michel Philippe, Michel Hocquaux, Henri Sebag, Irina Beck, and Jean P. Laugier A pharmaceutical or cosmetic composition for topical application comprises, in a physiologically acceptable support, the combination of benzoyl peroxide and at least one quaternary ammonium lipophilic salicylate having general formula (I): ##STRI## where: (i) R.sub.1, R.sub.2, R.sub.3 and R.sub.4 may be identical or different, representing a substituted or interrupted alkyl or cycloalkyl radical; (ii) R.sub.3 and/or R.sub.4 represent(s) the group: R.sub.8 —OC.sub.2 H.sub.3 R.sub.7].sub.n [OCH.sub.2 CHOH-CH.sub.2].sub.p where O.ltoreq.n.ltoreq.4 and p is 0 or 1; R.sub.8 represents H or an alkyl, alkenyl, alkylcycloalkyl or alkylanyl radical; (iii) R.sub.4 represents an alkylenephenyl radical; (iv), (v): R.sub.1 and R.sub.2 may form an aromatic or nonaromatic saturated or unsaturated heterocycle; (vi) R.sub.1, R.sub.2 and R.sub.3 together with nitrogen, may form polycyclic derivatives; and R.sub.5 represents a group having the formula: ##STR2## where n may vary from 0 to 10.

U.S. Pat. No. 5,023,090

Topical compositions containing LYCD and other topically active medicinal ingredients for the treatment of ACNE Robert H. Levin A topical composition comprising LYCD together with known topically active useful medicinal agents such as anti-wrinkling, antibiotic, anticancer, antifungal, anti-inflammatory such as anti-acne, antiviral, wound healing, and hair-growing agents. The LYCD works together with the other active agents to achieve a synergistic result more effective than can be obtained from the topical agents individually, and more effective than could be predicted from the mere addition of the known efficacies of the individual ingredients.

U.S. Pat. No. 4,446,145

Anti-microbial compositions for the topical treatment of acne vulgaris

Willem F. M. Van Bever

Novel compositions for the topical treatment of acne vulgaris said compositions comprising a pharmaceutically acceptable amount of benzoylperoxide and an anti-microbially effective amount of a suitable azole derivative.

Numerous innovations for a topical acne cream have been provided in the prior art that are adapted to be used. Even though these innovations may be suitable for the specific individual purposes to which they address, they would not be suitable for the purposes of the present invention as heretofore described.

SUMMARY OF THE INVENTION

The applicant has, surprisingly, discovered that particularly effective, stable compositions can be obtained for treatment of acne, cutaneous ulcers, warts and skin dyskeratinization, also for the general treatment of dermatoses and cutaneous disorders, wherein clotrimazole, betamethasone dipropionate and salicylic acid may be combined with binders, fillers, and emulsifiers is stable, does not decompose and remains active.

The applicant has established that when clotrimazole, betamethasone dipropionate and salicylic acid may be combined with binders, fillers, and emulsifiers in accordance with the invention, for example in a gel, the clotrimazole, betamethasone dipropionate and salicylic acid may be combined with binders, fillers, and emulsifiers had not degraded and remained stable after prolonged storage.

Because of the stability of the clotrimazole, betamethasone dipropionate and salicylic acid may be combined with binders, fillers, and emulsifiers, lower doses can be used in the compositions, thus in addition increasing cutaneous tolerance.

The applicants have also established that clotrimazole, betamethasone dipropionate and salicylic acid may be combined with binders, fillers, and emulsifiers absorb ultraviolet radiation to a certain extent. Thus compositions according to the invention exhibit fewer of the drawbacks generally encountered with the use of clotrimazole, betamethasone dipropionate and salicylic acid may be combined with binders, fillers, and emulsifiers, for example instability or secondary effects.

These novel compositions are, therefore, very stable and are tolerated well. They exhibit very good antibacterial properties without producing bacterial resistance, they are keratolytic and bacteriostatic, particularly towards Propionibacterium Acnes, one of the principal acne causing germs. They are also antiseptic, bactericidal, antifungal and are active in the treatment and reduction in the number of comedos.

Because of their properties, compositions according to the invention are suitable for treatment of cutaneous disorders and dermatoses, such as acne in particular, cutaneous ulcers, warts and skin dyskeratinization.

An object of the present invention is therefore a topical pharmaceutical and cosmetic composition containing clotrimazole, betamethasone dipropionate and salicylic acid may be combined with binders, fillers, and emulsifiers in an acceptable physiological support.

A further object of the invention concerns the method of use of the composition in the therapeutic treatment of acne.

A still further object of the invention is the provision of a composition and a method of cosmetic treatment.

Further objects of the invention will become apparent from the following description and examples.

It is an object of the present invention to provide topically applied pharmaceutical compositions suitable for the treatment of various ailments and physical conditions of the skin such as acne, bed sores, burns, infections, trauma, ulcers, wounds, and wrinkles.

It is a further object to provide compositions of the type described which are more effective than compositions presently known in the art.

It is a prime object of the invention to provide topical compositions of the type described for the treatment of acne, and more particularly, severe forms of acne, which compositions are more effective as remedies than the compositions presently known and used in the art.

The foregoing and other objects, advantages and characterizing features will become apparent from the following description of certain illustrative embodiments of the invention.

According to the invention, pharmaceutical compositions for topical application are provided by utilizing clotrimazole, betamethasone dipropionate and salicylic acid may be combined with binders, fillers, and emulsifiers in combination with known pharmaceutical agents or remedies. The clotrimazole, betamethasone dipropionate and salicylic acid may be combined with binders, fillers, and emulsifiers acts synergistically with the other agents to provide a composition having greater effectiveness than that of the individual agents, and a greater effectiveness than could be predicted by combining (in an additive fashion) the known or theoretical effectiveness of the individual ingredients.

According to the invention, it has been further found that many patients with severe acne, refractory to even long term treatment with a variety of the conventional acne remedies experience significant improvement in their acne condition within thirty days when treated twice daily with a combination of any of the conventional antibacterial ache medications and clotrimazole, betamethasone dipropionate and salicylic acid may be combined with binders, fillers, and emulsifiers.

It has been additionally found that mild to moderately severe acne can be treated and the condition ameliorated by the application of a topical pharmaceutical composition comprising clotrimazole, betamethasone dipropionate and salicylic acid may be combined with binders, fillers, and emulsifiers in a suitable vehicle, even in the absence of conventional acne remedies.

Accordingly, it is an object of the invention to provide a new topical treatment for acne and acneiform dermal disorders.

Another object of the invention is to provide a new topical treatment for acne which effectively adds to the armamentarium of physicians, and in particular dermatologists, to treat heretofore resistant forms of acne for which there was no safe, minimal side effect, and effective treatment available.

Another object of the invention is to provide a new topical treatment for acne which will avoid the undesirable side effects of the currently available oral antibiotics for the systemic treatment of acne and acneiform dermal disorders, such as diarrhea, abdominal cramping, nausea, vomiting, drug eruptions, photosensitivity, blood dyscrasia (e.g. depression of white blood cell count and red blood cell count), drug induced hepatitis (elevation of liver functions), and teratogenicity, to name a few.

Still another object of the invention is to provide a topical treatment for acne which uses an antibiotic that does not have the risk of bearing a toxic residue of a toxic bridging agent.

These and other objects are achieved by employing the principles of the invention wherein ampicillin, amoxicillin, another aminopenicillin, or other penicillin-like derivative is mixed with clotrimazole, betamethasone dipropionate and salicylic acid may be combined with binders, fillers, and emulsifiers and applied topically to the skin of a patient suffering from acne and other acneiform dermal disorders.

In accordance with the invention described herein, the term aminopenicillin is understood to be an aminopenicillin whose characteristic amino group is in the form of a primary amino group.

Further in accordance with the invention, a cephalosporin or cephalosporin derivative is mixed with clotrimazole, betamethasone dipropionate and salicylic acid may be combined with binders, fillers, and emulsifiers and applied topically to the skin of a patient suffering from acne and other acneiform dermal disorders. Suitable cephalosporins include cefadroxil, cefazolin, cephalexin, cephalothin, cephapirin, cephradine, cefaclor, cefamandole, cefonicid, ceforanide, cefotetan (a cephamycin), cefoxitin (a cephamycin), cefuroxime, the 1-acetyloxy ethyl ester of cefuroxime (cefuroxime axetil), cefoperazone, cefotaxime, ceftazidime, ceftin, ceftizoxime, ceftriaxone, and moxalactam (a 1-oxa-beta-lactam).

With the invention, a variety of treatment regimens are contemplated.

In a first treatment regimen, topical compositions of the invention are used alone to treat the acne and acneiform dermal disorders. In this respect, the topical compositions of the invention can be used as a first line treatment for acne and acneiform dermal disorders.

In a second treatment regimen of the invention, an orally administered antibiotic and a topical composition of the invention are used in combination. There are a number of specific courses of treatment that can be carried out in this second treatment regimen. The oral antibiotic and the topical composition of the invention can be administered simultaneously from the beginning. Or, the oral administration can be begun first, and the topical administration can then be begun. The oral administration can continue when the topical administration begins, or the oral administration can stop when the topical administration begins. Alternatively, the oral antibiotic and the topical composition of the invention can be administered sequentially. With sequential administration, oral administration can take place first, and then topical administration can be begun.

In this respect, after a conventional regimen of treating a patient for acne or acneiform dermal disorders with an orally administered antibiotic, such as tetracycline, minocycline, doxycycline, erythromycin, wherein the patient develops resistance or no improvement, it is the teaching of this invention that an antibiotic selected from the group consisting of ampicillin, amoxicillin, another aminopenicillin, penicillin-like derivatives, and cephalosporin, and derivatives and analogs thereof, is administered topically to the patient.

In a third treatment regimen of the invention, conventional topical medications and topical compositions of the invention can be administered simultaneously. The conventional topical medications which can be used include: benzoyl peroxide and/or topical tretinoin and/or any other topical agent currently used by physicians in the treatment of acne and acneiform dermal disorders.

In a fourth treatment regimen of the invention, conventional oral medications, conventional topical medications, and topical compositions of the invention can be administered simultaneously.

Although the inventors are not bound by any theoretical explanation as to why the compositions and the methods of the invention are efficacious in treating acne and acneiform dermal disorders, presentation of certain theoretical concepts may be of value.

For one thing, it is felt that the efficacy of the compositions and the methods of the invention is due in part to the clotrimazole, betamethasone dipropionate and salicylic acid may be combined with binders, fillers, and emulsifiers qualities of the compositions employed and the fact that a portion of the topically applied is absorbed by the skin and enters the patient's bloodstream.

Another possible reason for the efficacy of the compositions and the methods of the invention is that the compositions of the invention exert an anti-inflammatory effect on the cells of the sebaceous gland unit, thereby decreasing production of neutrophils and lymphocytes which contribute to inflammation.

Still another possible reason for the efficacy of the topical compositions and methods of the invention is that the topically applied clotrimazole, betamethasone dipropionate and salicylic acid may be combined with binders, fillers, and emulsifiers is able to kill microorganisms that cannot be killed by an orally administered antibiotic. More specifically, the topically applied clotrimazole, betamethasone dipropionate and salicylic acid may be combined with binders, fillers, and emulsifiers directly kills microorganisms in the sebaceous follicle that are shielded by a hydrophobic sebaceous film inside the follicle from the effects of an antibiotic in the bloodstream. The bloodstream is essentially an aqueous medium, and the hydrophobic sebaceous film blocks the clotrimazole, betamethasone dipropionate and salicylic acid may be combined with binders, fillers, and emulsifiers in the bloodstream, from diffusing onto the microorganisms on the other side of the sebaceous film. However, the microorganism may produce products that are fat soluble and are able to cross through the sebaceous film and thereby irritate the cells lining the sebaceous follicle. Thus, the hydrophobic sebaceous film may allow passage, in one direction, of irritants from the microorganisms to the follicle walls, but the hydrophobic sebaceous film prevents passage of clotrimazole, betamethasone dipropionate and salicylic acid may be combined with binders, fillers, and emulsifiers in the bloodstream from diffusing across the hydrophobic sebaceous film in the other direction to the microorganisms.

The novel features which are considered characteristic for the invention are set forth in the appended claims. The invention itself, however, both as to its-construction and its method of operation, together with additional objects and advantages thereof, will be best understood from the following description of the specific embodiments when read and understood in connection with the accompanying drawing.

BRIEF LIST OF REFERENCE NUMERALS UTILIZED IN THE DRAWING

Figure 1:
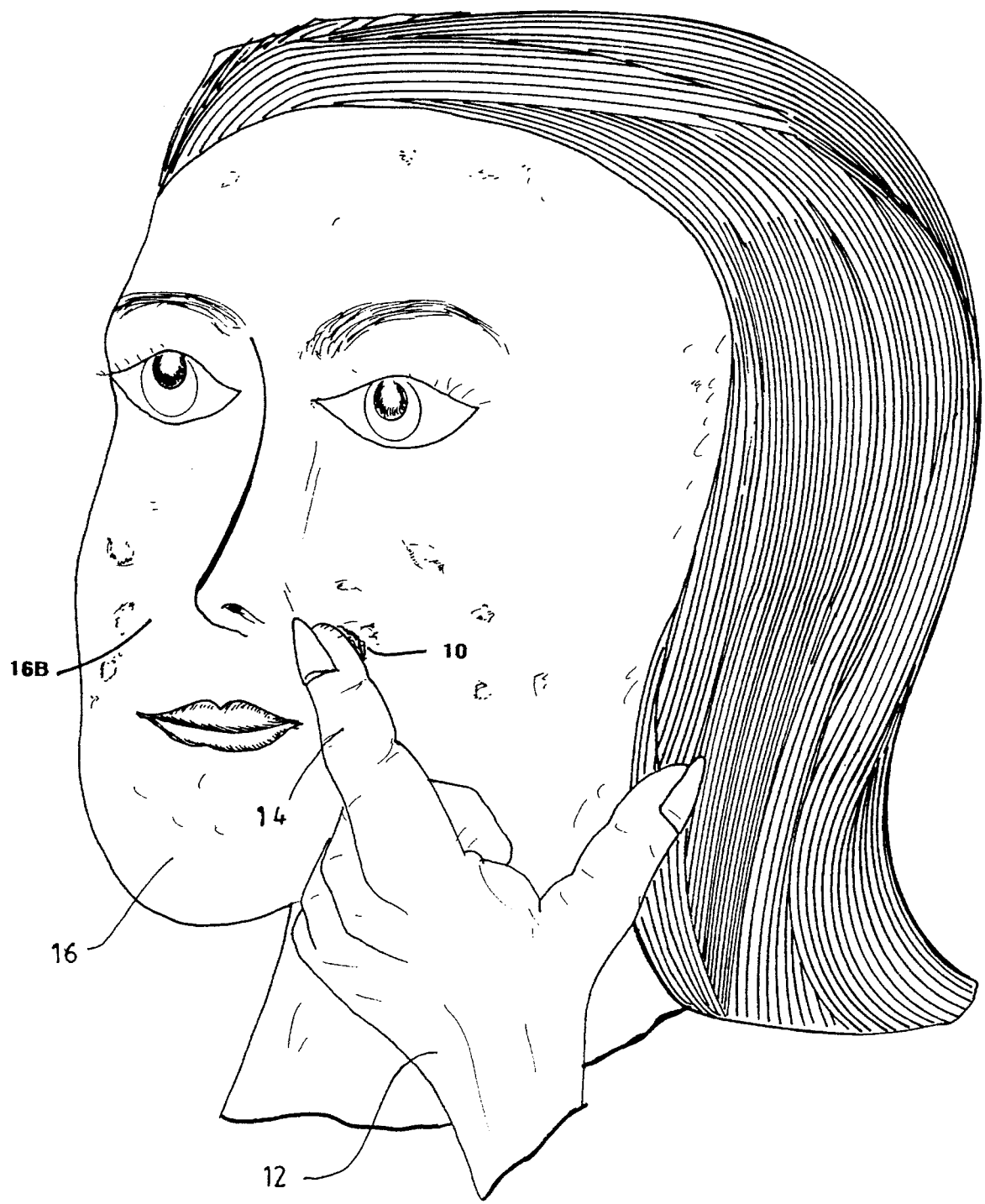
FIG. 1 is a perspective view of a person applying a topical acne cream to her face

10 -acne cream 10
12 - hand 12
14 - finger 14
16A -acne in remission 16A
16B - active acne 16B
18 - clortrimazole 18
20 - betamethasone 20
22 - salicylic acid 22
24 - binder 24
26 - filler 26
28 - emulsifier 28

DETAILED LIST OF REFERENCE NUMERALS UTILIZED IN THE DRAWING

10 -acne cream 10 is composed of primary ingredients such as: clortrimazole 18; betamethasone 20; and salicylic acid 22 having secondary optional ingredients such as: binder 24; filler 26; and emulsifier 28

12 - hand 12 is utilized by person to apply topical acne cream 10 by placing the cream on a finger 14 and rubbing it thoroughly into acne 16A and/or 16B 14 - finger 14 is utilized to apply topical acne cream 10 onto acne 16A and 16B 16A -acne in remission 16A has been previously treated with topical acne cream 10 which has reduced the inflammation by virtue of one of its primary ingredients, betamethasone 20, and anti-fungal properties exhibited by clortrimazole 18, the anti-septic and anti-bacterial properties is by the salicylic acid 22

16B - active acne 16B which will reduce the inflammation by virtue of one of its primary ingredients, betamethasone 20, and antifungal properties exhibited by clortrimazole 18 and anti-septic properties of salicylic acid 22

18 - clortrimazole 18 is an anti-fungal ingredient usually termed fungicidal due to its characteristic of killing fungus when they come in contact with the substance 20 - betamethasone 20 is an anti-inflammatory ingredient due to its characteristic of reducing inflammation when they come in contact with the substance 22 - salicylic acid 22 is an anti-septic/keratolytic substance which rapidly reduces inflammation caused by a person's body's immune reaction to acne bacteria

DETAILED DESCRIPTION OF THE PREFERRED EMBODIMENT

Firstly, referring to FIG. 1 which is a perspective view of a person applying a topical acne cream to her face exhibiting the following features: 10 -acne cream 10 is composed of primary ingredients such as: clortrimazole 18; betamethasone 20; and salicylic acid 22 having secondary optional ingredients such as: binder 24; filler 26; and emulsifier 28; hand 12 is utilized by person to apply topical acne cream 10 by placing the cream on a finger 14 and rubbing it thoroughly into acne 16A and/or 16B; finger 14 is utilized to apply topical acne cream 10 onto acne 16A and 16B; acne in remission 16A has been previously treated with topical acne cream 10 which has reduced the inflammation by virtue of one of its primary ingredients, betamethasone 20, and anti-fungal properties exhibited by clortrimazole 18 and antiseptic/keratolytic properties of salicylic acid 22; and active acne 16B which will reduce the inflammation by virtue of one of its primary ingredients, betamethasone 20, and anti-fungal properties exhibited by clortrimazole 18 and antiseptic properties exhibited by salicylic acid 22. When the topical acne cream 10 is applied to active acne 16B, the primary ingredients absorb into the skin through spaces between the cells as well as into the sebaceous glands and hair follicles, thus, permitting the active ingredients to come in direct contact with the active acne 16A which is caused by bacteria usually being of the Staphylococcus species. The two primary active ingredients: salicylic acid 22 perform a bacteriocidal means whereby the active bacteria are killed, the clortrimazole 18 kills any fungus. The other primary ingredient, betamethasone 20, produces an anti-inflammatory effect which has been caused by a person's body reaction to bacteria whereby the white blood cells of the immune system release histamine which results in inflammation and its characteristic reddening appearance.

Figure 2:
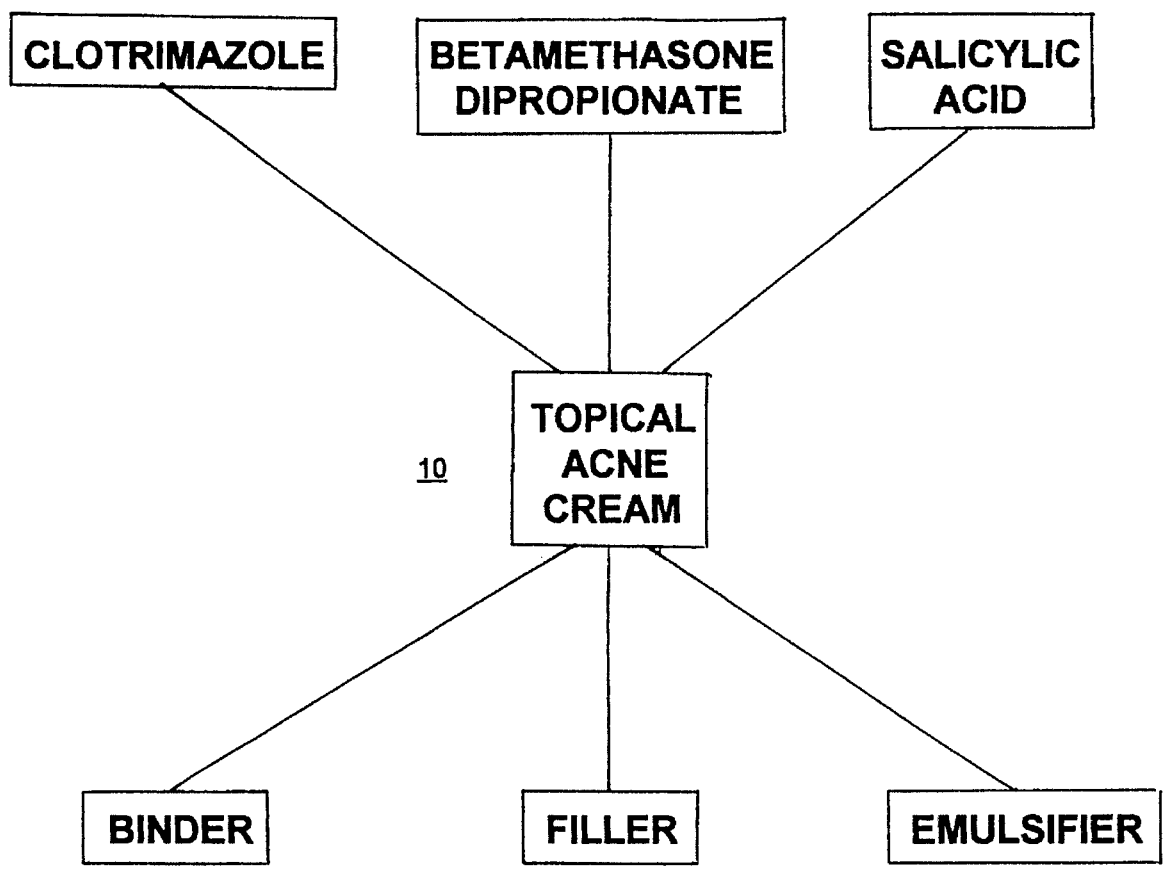
FIG. 2 is a flow diagram of the primary and secondary ingredients utilized in the acne cream

Referring now to FIG. 2 which is a flow diagram of the primary and secondary ingredients utilized in the acne cream exhibiting the following features: clortrimazole 18 is an anti-fungal ingredient usually termed fungicidal due to its characteristic of killing fungus when they come in contact with the substance; betamethasone 20 is an anti-inflammatory ingredient due to its characteristic of reducing the inflammed area when they come in contact with the substance; salicylic acid 22 is an anti-septic/keratolytic substance which rapidly reduces inflammation caused by a person's body's immune reaction to acne bacteria; binder 24 is a non-essential secondary ingredient which may be present in the topical acne cream 10 having the function to maintain all ingredients in the emulsion cream for prolonged time periods; filler 26 is a nonessential secondary ingredient which may be present in the topical acne cream 10 having the function to add bulk to the cream since the active primary ingredients are so concentrated that only a minute amount is required fir topical treatment; and emulsifier 28 is a non-essential secondary ingredient which may be present in the topical acne cream 10 having the function to permit the mixing and suspension of non-similar physical characteristic active, primary, and secondary ingredients.

It will be understood that each of the elements described above, or two or more together, may also find a useful application in other types of constructions differing from the type described above.

While the invention has been illustrated and described as embodied in a topical acne cream, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A topical acne cream consisting of:
   a) clortrimazole in a concentration of 0.1% to 99.8%;
   b) salicylic acid in a concentration of 0.1% to 99.8%;
   c) betamethasone in a concentration of 0.1% to 99.8%;
   d) a binder selected from the group consisting of pectin, protein, and chitin in a concentration of 0.1% to 99.7%; and
   e) a filler selected from the group consisting of petroleum jelly, vegetable oil, animal oil, and natural oil in a concentration of 0.1% to 99.7.

\* \* \* \* \*